US00PP30453P2

(12) United States Plant Patent
de Jong

(10) Patent No.: US PP30,453 P2
(45) Date of Patent: Apr. 30, 2019

(54) ***HYDRANGEA* PLANT NAMED 'JON04'**

(50) Latin Name: *Hydrangea macrophylla*
Varietal Denomination: JON04

(71) Applicant: Jos de Jong, Boskoop (NL)

(72) Inventor: Jos de Jong, Boskoop (NL)

(73) Assignee: DeJong Plant BV (NL)

( * ) Notice: Subject to any disclaimer, the term of this patent is extended or adjusted under 35 U.S.C. 154(b) by 0 days.

(21) Appl. No.: 15/732,652

(22) Filed: Dec. 7, 2017

(51) Int. Cl.
*A01H 5/00* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'JON04' is disclosed, characterized by a red mophead inflorescence and dark green foliage strongly flushed greyed-purple. Plants are compact and well-branched, forming dense, attractive plants. The new variety is a *Hydrangea*, normally produced as an ornamental plant for containers or gardens.

1 Drawing Sheet

Latin name of the genus and species: *Hydrangea macrophylla.*

Variety denomination: 'JON04'.

BACKGROUND OF THE INVENTION

The new *Hydrangea* cultivar is a product of a planned breeding program conducted by the inventor, Jos de Jong in the Netherlands. The objective of the breeding program was to identify new *Hydrangea* varieties with darker foliage. The mutation resulting in the new variety was discovered by the inventor during August of 2012 at a commercial nursery in Boskoop, the Netherlands.

The parent is the unpatented commercial variety *Hydrangea macrophylla* 'Black Diamond Baroque Angel'. The inventor grew large quantities of plants of the parent variety and selected for naturally occurring branch mutations with darker foliage and different flower colors.

Asexual reproduction of the new cultivar 'JON04' by softwood cuttings was first performed during the Summer of 2012 at a commercial greenhouse in Boskoop, the Netherlands. Subsequent propagation has shown that the unique features of this cultivar are stable and reproduced true to type in two successive generations.

SUMMARY OF THE INVENTION

The cultivar 'JON04' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JON04'. These characteristics in combination distinguish 'JON04' as a new and distinct *Hydrangea* cultivar:

1. Mop-head inflorescence.
2. Compact plant form.
3. Well branched growth habit.
4. Red colored inflorescence.
5. Dark green foliage prominently flushed greyed purple.

PARENT COMPARISON

Plants of the new cultivar 'JON04' are similar to plants of the parent in most horticultural characteristics, however, plants of the new cultivar 'JON04' differ in the following:

1. The new variety has darker foliage than the parent variety, with more purple flushing.

COMMERCIAL COMPARISON

'JON04' can be compared to the commercial variety *Hydrangea* 'Jon03', U.S. Plant patent application Ser. No. 15/732,653, filed concurrently. These varieties are similar in most horticultural characteristics; however, 'JON04' differs in the following:

1. 'Jon04' has red flowers, whereas flowers of 'Jon03' are mauve pink.

'JON04' can be compared to the commercial variety *Hydrangea* 'Jon02', U.S. Plant patent application Ser. No. 15/732,651, filed concurrently. These varieties are similar in most horticultural characteristics; however, 'JON02' differs in the following:

1. 'Jon04' has red flowers, 'Jon02' has deep vibrant pink flowers.

BRIEF DESCRIPTION OF THE PHOTOGRAPH

The accompanying photograph illustrates in full color a typical flowering plant of 'JON04' grown in a greenhouse in the Netherlands. Age of the plant photographed is approximately 1.5 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The 2007 Royal Horticultural Society Colour Chart except where general terms of ordinary dictionary significance are used. The following observations and measurements describe 'JON04' plants grown in a greenhouse, in the Netherlands. The growing temperature ranged from approximately 18° C. to 27° C. daytime and 5° to 10° C. at night. Measurements and numerical values represent averages of typical plant types. Measurements were taken during July of 2017.

Botanical classification: *Hydrangea macrophylla* 'JON04'.

PROPAGATION

Time to initiate roots: Approximately 16 to 28 days at approximately 22 to 27° C.

Root description: Thick and fine, freely root branching and dense, fibrous. White to tan, not accurately measured with The R.H.S. Chart.

Propagation method: Softwood cuttings.

PLANT

Age of plant described: About 8 months.

Pot size: 1 gallon.

Growth habit: Flowering perennial shrub. Upright, non-climbing.

Overall plant shape: Round.

Height: About 30 to 32 cm.

Plant spread: About 33 to 41 cm.

Growth rate: Moderate.

Plant vigor: Moderate.

Branching characteristics: Opposite, basal branches, some pinching required. Non-fasciated.

Length of lateral branches/stems: Approximately 15 to 30 cm on an 8 month old plant.

Number of lateral branches: Varies, depending upon pinching. On average 8 on an 8 month old plant.

Diameter of lateral branches: 6 mm.

Lateral branch shape and appearance: Round.

Lateral branch strength: Good.

Internode length: Average 5 to 7 cm.

Branch/stem color: Immature: Near RHS Yellow-Green 144C, faint flushing at nodes near Greyed-Purple N186A. Mature: Near RHS Green 139A flushed Greyed-Purple N186A.

Branch/stem texture: Glabrous, lenticels not observed.

Branch angle: 0 to about 30°.

Branch pubescence: No.

FOLIAGE

Leaf:

*Arrangement*.—Opposite.

*Average length*.—10 to 15 cm.

*Average width*.—7 to 8 cm.

*Shape of blade*.—Ovate, without lobes.

*Apex*.—Acute.

*Base*.—Rounded to broad tapered.

*Margin*.—Crenate.

*Texture and appearance of top surface*.—Leathery, slightly glossy.

*Texture and appearance of bottom surface*.—Matte, reticulate veins.

*Color*.—Solid, non-variegated. Young foliage upper side: Near RHS Green 139A flushed Greyed-Purple N186B. Young foliage under side: Near RHS Green 137A. Mature foliage upper side: Near RHS Greyed-Green N189A, flushed Greyed-Purple N186B. Mature foliage under side: Near RHS Green 137A.

*Venation*.—Type: Pinnate. Venation color upper side: Near RHS Yellow-Green 144C. Venation color under side: Near Yellow-green 145A.

Petiole:

*Average length*.—2.0 cm.

*Diameter*.—7 mm.

*Color*.—Upper side: Near RHS Yellow-green 145A. Under side: Near RHS Yellow-green 145B.

*Texture upper side*.—Glossy, glabrous.

*Texture under side*.—Glossy, glabrous.

FLOWER

Bloom period:

*Natural season*.—June to October in the Northern hemisphere.

Inflorescence:

*Arrangement*.—Terminal corymb.

*Commercial type*.—Mophead.

*Infloresence shape*.—Half-sphere.

*Panicle height*.—8 to 12 cm.

*Panicle diameter*.—9 to 15 cm.

*Quantity of flowers per inflorescence*.—Fertile flowers not observed to date. Sterile Flowers: 18 to 24 average range.

*Persistent or self-cleaning*.—Persistent.

*Fragrance*.—None.

Sterile flower:

*Bud shape*.—Globular.

*Bud length*.—5.0 mm.

*Bud diameter*.—5.0 mm.

*Bud color*.—Near RHS Yellow-Green N144B flushed Red 46C.

*Flower aspect*.—Upright and outward.

*Flower shape*.—Cruciform if 4 sepals, slightly overlapping whorl if 5 sepals.

*Flower diameter*.—Average range 22 to 35 mm.

*Flower depth*.—28 mm.

*Aspect*.—Upwardly cupped.

Sterile flower sepals:

*Sepal arrangement*.—Cruciform if 4 sepals, slightly overlapping whorl if 5 sepals.

*Sepal number*.—4 or 5.

*Length of sepal*.—Approximately 1.8 to 2.5 cm.

*Width of sepal*.—Approximately 1.3 cm.

*Angel of attachment/aspect*.—Sepals angled upward approximately 25° to 45° from point of attachment. Sepals upwardly cupped.

*Apex*.—Broad Acute.

*Shape of sepal*.—Deltate.

*Sepal margin*.—Shallow crenate.

*Sepal base*.—Obtuse.

*Sepal texture*.—Smooth, upper and under sides.

*Color*.—Upper surface at first opening: Near RHS Red 46C, base Yellow-White 158D. Upper surface at maturity: Near RHS Red 45D. Under surface at first opening: Near RHS Red 46C. Under surface at maturity: Near RHS Red 45C. Color when fading: Upper and lower surfaces: Near RHS Red 46D.

Sterile flower petal: Not observed.

Sterile flower pedicel:

*Length*.—10 to 14 mm.

*Diameter*.—1 mm.

*Angle*.—Upright and outward.

*Strength*.—Flexible, not prone to breakage.

*Texture*.—Smooth.

*Color*.—Near RHS Yellow-Green 147A.

Fertile flower: Not observed to date.

REPRODUCTIVE ORGANS

Sterile flower: All reproductive parts irregular and malformed, reduced to less than 1 mm or not present.

OTHER CHARACTERISTICS

Disease resistance: Neither resistance nor susceptibility to diseases or pests has been observed in this variety.

Cold tolerance: −24° C. to 38° C.

Fruit/seed production: Not observed to date.

What is claimed is:

1. A new and distinct cultivar of *Hydrangea* plant named 'JON04' as herein illustrated and described.

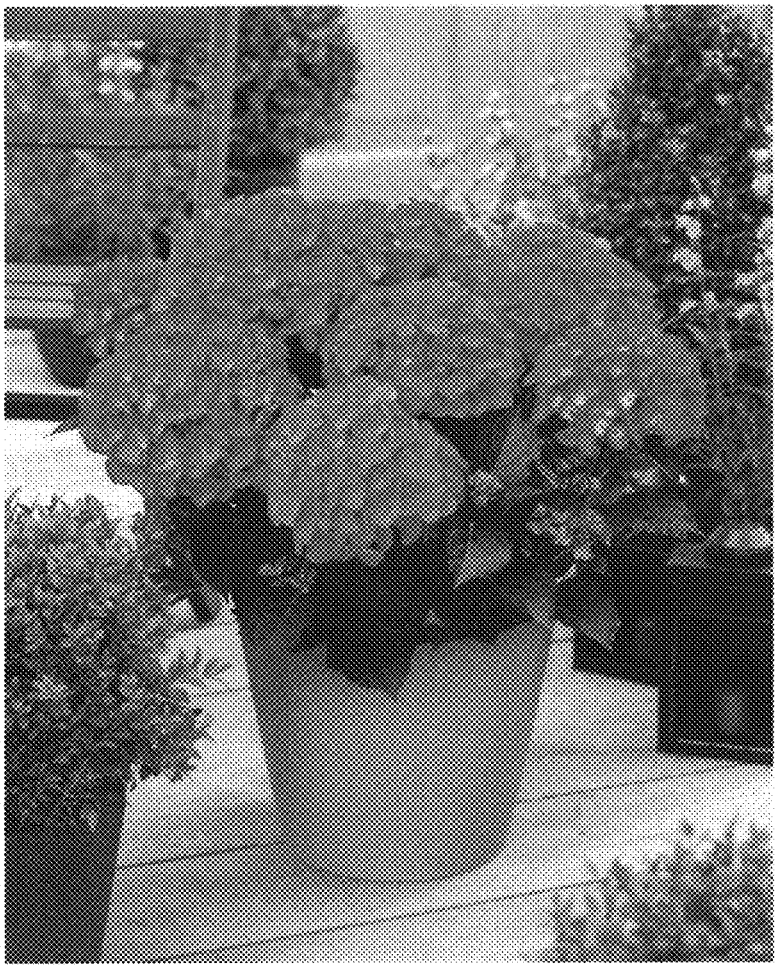

* * * * *